(12) United States Patent
Makdissi et al.

(10) Patent No.: US 11,229,800 B2
(45) Date of Patent: Jan. 25, 2022

(54) PIEZOELECTRIC ENERGY HARVESTER INCLUDING A MONITORING CIRCUIT FOR DETECTING HARVESTER ALTERATION OR DOWNGRADING

(71) Applicant: CAIRDAC, Antony (FR)

(72) Inventors: Alaa Makdissi, Paris (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 563 days.

(21) Appl. No.: 16/351,506

(22) Filed: Mar. 12, 2019

(65) Prior Publication Data

US 2020/0289830 A1    Sep. 17, 2020

(51) Int. Cl.
*H02N 2/18* (2006.01)
*A61N 1/378* (2006.01)
*A61N 1/05* (2006.01)

(52) U.S. Cl.
CPC ............ *A61N 1/378* (2013.01); *A61N 1/059* (2013.01); *H02N 2/181* (2013.01); *H02N 2/188* (2013.01)

(58) Field of Classification Search
CPC ........ H02N 2/181; H02N 2/188; H02N 2/185; H02N 2/183; A61N 1/378; A61N 1/3785; A61N 1/059; A61N 1/3756; A61N 1/37217; A61N 1/37518; A61N 1/37512; H01L 41/113; H01L 41/1134
See application file for complete search history.

(56) References Cited

U.S. PATENT DOCUMENTS

| | | | |
|---|---|---|---|
| 2008/0200963 A1* | 8/2008 | Pless | A61N 1/0587 607/36 |
| 2010/0186493 A1 | 7/2010 | Brusarosco et al. | |
| 2014/0128932 A1* | 5/2014 | Ewert | A61N 1/37252 607/18 |
| 2016/0275771 A1 | 9/2016 | Visweswara et al. | |
| 2017/0084815 A1 | 3/2017 | Choo et al. | |
| 2018/0021570 A1* | 1/2018 | An | A61N 1/37512 607/123 |
| 2018/0116540 A1* | 5/2018 | Kharam | A61N 1/37205 |
| 2018/0149623 A1 | 5/2018 | Notohardjono et al. | |
| 2020/0094048 A1* | 3/2020 | Regnier | A61B 5/6861 |
| 2020/0147396 A1* | 5/2020 | Sheldon | A61N 1/37282 |
| 2020/0338241 A1* | 10/2020 | Regnier | A61L 31/026 |
| 2021/0023377 A1* | 1/2021 | Muessig | A61N 1/36542 |

\* cited by examiner

*Primary Examiner* — J. San Martin
(74) *Attorney, Agent, or Firm* — Steven Greenberg, Esq.; Shutts & Bowen LLP

(57) ABSTRACT

The energy harvesting module is provided with a pendular unit comprising an inertial mass coupled to an elastic piezoelectric beam providing a power voltage. An acceleration sensor provides a signal representative of the instantaneous acceleration of the beam in a direction perpendicular to a surface of the beam, and an angular speed sensor provides a signal representative of the instantaneous angular speed of rotation of the beam about an axis perpendicular to a plane of bending of the beam. Based on the voltage, acceleration and angular speed values, a beam integrity monitoring circuit estimates parameters of a mechanical-electrical transfer function and derives therefrom metrics representative of physical and electrical parameters of the pendular unit and of the material of the beam. This makes it possible to evaluate the proper operation of the energy harvester and to detect a potential performance decrease liable to lead to a failure in the more or less short term.

13 Claims, 4 Drawing Sheets

PIEZOELECTRIC ENERGY HARVESTER INCLUDING A MONITORING CIRCUIT FOR DETECTING HARVESTER ALTERATION OR DOWNGRADING

BACKGROUND OF THE INVENTION

Field of the Invention

The invention relates to energy harvesting devices, also known as harvesters or scavengers, which collect the mechanical energy resulting from various movements they undergo and convert this mechanical energy into electrical energy.

It more particularly relates to harvesters of the "PEH" (Piezoelectric Energy Harvester) type, which use as a mechanical-electrical transducer an oscillating piezoelectric beam coupled to an inertial mobile mass.

The invention will be more particularly described in an application of such energy harvesters to autonomous medical devices, in particular devices of the autonomous implantable capsule type, in particular those which are intended to be implanted in a cardiac cavity.

This application, although being particularly advantageous, must however not be considered as limitative of the invention, whose teachings may be applied to many other types of autonomous devices incorporating an energy harvester of the PEH type, whether these devices are implantable or not, medical or not.

Description of the Related Art

In the field of medical implants, recent advances in miniaturization of active devices and advances in life sciences allow from now on the development of a wide variety of fully autonomous, miniaturized implantable systems for monitoring, diagnosis or treatment purposes. Such devices involve less invasive implantation procedures, provide more comfort, increased performances, and often open up access to new types of diagnoses and treatments.

When applied to the field of medical implants, the invention more particularly relates to those devices which incorporate a self-powering system comprising a mechanical energy harvester associated with an integrated energy storage component, such as a rechargeable battery or a high-performance capacitor.

Indeed, one of the critical aspects of these miniaturized devices is the power autonomy. The life duration of such an implant being of about 8-10 years, taking into account the very small dimensions, it is not possible to use a conventional battery, even a high-density one.

The energy harvesting device, also known as an harvester or a scavenger, addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, vibrations of the cardiac tissues linked i.a. to closings and openings of cardiac valves, or blood flow rate variations in the surrounding environment, which stress the implant and make it oscillate at the rhythm of the flow rate variations.

The mechanical energy collected by the harvester is converted into electrical energy (voltage or current), by means of a suitable mechanical-electrical transducer, for powering the various circuits and sensors of the device and for charging the energy storage component. This powering system allows the device to operate in full power autonomy during its whole life.

This energy harvesting technique is particularly well adapted for powering the implanted autonomous capsules having no physical connection with a remote device. These capsules are called for this reason "leadless capsules", for distinguishing them from the electrodes or sensors arranged at the distal end of a lead, through the full length of which run one or several conductors connected to a generator connected to the opposite, proximal end.

The invention is nevertheless not limited to a particular type of capsule, nor to a leadless implant, and it is applicable as well to many other types of implantable medical devices, whatever the operational purpose thereof, cardiac or other, medical or not.

In the cardiac application case, the leadless capsule continuously monitors the rhythm of the patient and if necessary issues to the heart electrical pulses for stimulation, resynchronization and/or defibrillation in case of rhythm disorders detected by the capsule. The leadless capsule may be an epicardial capsule, fixed to the outer wall of the heart, or an endocavitary capsule, fixed to the inner wall of a ventricular or atrial cavity, or a capsule fixed to the wall of a vessel near the myocardium. The fixation of the capsule to the implantation site is made through a protruding anchoring system extending the capsule body and designed to penetrate the cardiac tissue, in particular by means of a screw.

The capsule further comprises various electronic circuits, sensors, etc., as well as wireless communication emitter/receiver means for the remote exchange of data, the whole being integrated in a body of very small size that can be implanted at sites whose access is difficult or that leave little space available, such as the apex of the ventricle, the inner wall of the atrium, etc.

WO 2019/001829 A1 (Cairdac) describes an example of such a leadless intracardial capsule.

There exist several types of energy harvesters, based on various physical principles: system of the automatic wind-up watch movement type, mobile magnet system, bellows system or similar system collecting blood pressure variations, etc.

The invention more particularly relates to capsules or similar implantable devices whose energy harvester uses an inertial pendular unit subjected to the above-described external stresses.

An inertial pendular unit implements a transducer including in the capsule a mobile mass, called "seismic mass" or "inertial mass", which is driven according to the movements of the capsule, permanently subjected to the various external stresses described hereinabove. After each of these stresses, the inertial mass, which is coupled to an elastically deformable element, oscillates at a natural frequency of free oscillation.

The mechanical energy of the oscillation is converted into electrical energy by a mechanical-electrical transducer issuing an electrical signal. This signal is provided to a power management circuit of the capsule, which rectifies and regulates the electrical signal to output a stabilized direct voltage or current, for powering the various electronic circuits and sensors of the implant, as well as for charging the energy storage component.

The mechanical-electrical transducer may be in particular a piezoelectric component cyclically and alternately stressed in bending so as to generate within its constituent material electrical charges that are collected at the surface of the component to be used by the self-powering system of the leadless capsule. This piezoelectric component may in particular be a piezoelectric beam clamped at one of its end and coupled to the inertial mass at its other end, which is free.

Such an energy harvester for powering an implant from the oscillations of a piezoelectric beam, or "PEH" (Piezoelectric Energy Harvester), is described in particular in U.S. Pat. No. 3,456,134 A (Ko) and in above-mentioned WO 2019/001829 A1.

It will be noted that the term "beam" has to be understood in its widest meaning, i.e. an elongated, thin and flat strip, it being understood that the shape of this strip is not necessarily rectangular nor its thickness constant (as in the description of the particular embodiment that will be given hereinafter). Within the meaning of the present invention, the term "beam" hence covers elements that may have a width and/or a thickness that are not constant in the longitudinal direction, as well as, possibly, a deformability going beyond a single degree of freedom in bending.

The starting point of the invention is the necessity to be able to check at regular intervals the "health condition" of the PEH, especially the absence of ageing or degradation of the piezoelectric beam that could significantly affect the level of energy provided by the PEH, and therefore the whole operation of the implant.

Specifically, the production of energy by piezoelectric beam bending involves permanently oscillating, and hence deforming, the latter, during the whole expected life of the implant, which is typically of at least 10 years (i.e. about 400 million heartbeats), and can even reach 15 to 20 years.

At each heartbeat, the pendular unit oscillates several times at its natural frequency, typically of the order of a few tens of hertz, with bounces of decreasing amplitude, characteristic of a damped periodic oscillation, up to the following heartbeat where the stress/oscillation cycle is similarly repeated. Specifically, the first two oscillations of the pendular unit are those that, due to their high amplitude, most stress the beam and create the most fatigue within the material of the latter.

Due to their permanent and repeated character, the repeated stresses undergone by the beam during the whole life duration of the PEH cause an ageing of the piezoelectric material, which consequently modify the physical-electrical parameters of the latter in a manner that is deleterious to the piezoelectric beam integrity, in particular by a lower bending stiffness and a degradation of the mechanical-electrical conversion coefficient.

There exists a need to be able to control the integrity of the beam during the whole life duration of the implant, this integrity being essential to the preservation of the level of quality of the mechanical-electrical conversion. In case of observed decrease of the PEH performances, it will then be possible to emit an alert or at the very least to anticipate a risk of failure in the more or less short term.

It is known to measure, by various static or dynamic techniques that will be described hereinafter, the physical and electrical characteristics of a beam made of piezoelectric material, such as a clamped/free beam stressed in bending.

However, these techniques are laboratory techniques, implemented on a test bench, that further presuppose that the beam is not subjected to any external stress other than those of the laboratory device.

These techniques are hence not transposable to the control in situ of the integrity of a beam of a PEH in operation and integrated into the implanted capsule. Indeed, on the one hand, it is not possible to connect the PEH beam to external measurement instruments, and on the other hand, the beam is continuously stressed by the movements of the capsule at the implantation site, which excludes in particular techniques such as the measurements of complex impedance requiring the controlled application of specific vibratory frequencies to the beam.

Another difficulty lies in the fact that it must be possible to autonomously monitor the proper operation of the PEH within the capsule, and that this monitoring will hence consume a certain quantity of energy for being implemented, energy that will have to be taken from the energy wholly produced by the PEH itself. Actually, this monitoring shall not be done to the detriment of the powering of the electronic circuits of the capsule, and shall hence not involve a too high consumption of energy (typically, no more than 5 to 10% of the total energy budget of the PEH shall be dedicated to the monitoring of the proper operation of the latter).

One of the objects of the invention is to propose a means for monitoring in situ the beam integrity and the proper operation of the PEH, which means is free from all these limitations and can be implemented after implantation of the capsule and taking into account that the latter is not accessible from the outside and will continue to be stressed by multiple external effects resulting from the heartbeats and the blood flows in the surrounding medium.

BRIEF SUMMARY OF THE INVENTION

More precisely, the invention proposes for that purpose an energy harvesting module, comprising:
  a pendular unit subjected to external stresses applied to the module, the pendular unit comprising a beam that is elastically deformable in bending according to at least one degree of freedom, with a clamped end and an opposite free end coupled to an inertial mass,
  wherein the beam is a piezoelectric beam forming a mechanical-electrical transducer adapted to convert into an oscillating electrical signal a mechanical energy produced by oscillations of the pendular unit; and
  a power management circuit, adapted to rectify and regulate the oscillating electrical signal to output a stabilized direct power voltage or current.

The energy harvesting module further comprises a circuit for monitoring the integrity of the beam, comprising:
  an acceleration sensor for providing an acceleration signal representative of the instantaneous acceleration of the beam in a direction perpendicular to a surface of the beam;
  a collecting and sampling circuit, adapted to receive the oscillating signal and the acceleration signal, and to provide a plurality of successive samples each containing an oscillating signal value associated with a concomitant acceleration value;
  a memory storing a transfer function describing the mechanical-electrical behavior of the beam,
  wherein said transfer function is a relation providing, for respective given values of a set of modelling parameters, an oscillating signal value as a function of a value of instantaneous acceleration of the beam; and
  a processor and a memory comprising instructions for causing the processor to execute a process comprising the following steps: a) receiving the plurality of said successive samples each containing an oscillating signal value associated with a concomitant acceleration value; b) applying these successive samples to said transfer function to derive therefrom a corresponding set of estimates of said modelling parameters from the oscillating signal and acceleration values of the successive samples; and c) deriving from said estimates of the modelling parameters at least one physical metric of the pendular unit and/or of the beam.

According to various preferential subsidiary features:

the at least one physical metric is a metric of the group comprising: resonance frequency $F_n$ of the pendular unit; quality factor Q of the pendular unit; generalized coupling coefficient Θ of the pendular unit; electric capacitance C of the beam; mechanical stiffness $E_p$ of the beam; and mechanical-electrical conversion coefficient $e_{31}$ of the beam;

the beam integrity monitoring circuit further comprises an angular speed sensor for providing an angular speed signal representative of the instantaneous angular speed of rotation of the beam about an axis perpendicular to a plane of bending of the beam, the transfer function is a relation further providing the oscillation signal value as a function of a value of instantaneous angular speed of the beam, the collecting and sampling circuit is adapted to further receive the angular speed signal, the successive samples provided by the collecting and sampling circuit each contain an oscillating signal value associated with concomitant acceleration and angular speed values, and at step b) the process derives the set of estimates of the modelling parameters from the oscillating signal, acceleration and angular speed values of the successive samples; the beam integrity monitoring circuit further comprises a switch for disconnecting said power management circuit during a predetermined period of activation of the collecting and sampling circuit, in particular a period at least three times longer than a period of natural oscillation of the pendular unit;

at step c), the process comprises the following steps: c1) deriving a set of first metrics specific to the pendular unit from said estimates of the modelling parameters; and c2) deriving from a set of second metrics specific to the beam from said first metrics determined at step c1);

the process further comprises memorizing, into an history, the values of the first metrics determined at step c1) and/or of the second metrics determined at step c2);

the process further comprises comparing the first metrics determined at step c1) and/or the second metrics determined at step c2) with respect to respective reference values;

the process further comprises analyzing the evolution over time of the first metrics determined at step c1) and/or the second metrics determined at step c2);

the sampling frequency of the collecting and sampling circuit is higher than 200 Hz.

The module may advantageously be incorporated into an autonomous device housing, in a device body: an electronic unit; said energy harvesting module; and an energy storage component for powering the electronic unit, and wherein said stabilized direct voltage or current output by the power management circuit is used to power the electronic unit and/or to charge the energy storage component.

The autonomous device may in particular be an active medical device, in particular an implantable autonomous capsule, comprising a capsule body provided with an element for its anchoring to a wall of a patient's organ, and wherein said external stresses to which is subjected the pendular unit are stresses applied to the capsule body under the effect of movements of said wall and/or of blood flow rate variations in the surrounding medium.

BRIEF DESCRIPTION OF THE DRAWINGS

The foregoing and other objects, aspects and advantages of the invention will be better understood from the following detailed description of a preferred embodiment of the invention with reference to the appended drawings, in which the same numerals refer to identical or functionally similar features over the various figures.

DETAILED DESCRIPTION OF A PREFERRED EMBODIMENT OF THE INVENTION

An exemplary embodiment of the device of the invention will now be described, in an application to an autonomous implantable capsule intended to be implanted into a cardiac cavity.

As indicated hereinabove, this particular application is not limitative of the invention, whose teachings may be applied to many other types of autonomous devices incorporating an energy harvester of the PEH type, whether these devices are implantable or not, medical or not.

As regards software aspects thereof, the invention may be implemented by a suitable programming of the leadless capsule control software. The adaptation of these devices to implement the invention is within the reach of the one skilled in the art, and it won't be described in detail. In particular, it will be possible to adapt the software programs stored in memory and executed, and to use them to implement the functions of the invention that will be described hereinafter. The method of the invention implements software means, using suitable algorithms executed by a microcontroller or a digital signal processor. For the sake of clarity, the various processings applied will be decomposed and schematized by a number of distinct modules or functional blocks and/or interconnected circuits, but this representation is however only illustrative, these functions or circuits having common elements and corresponding in practice to a plurality of functions globally executed by a same software program.

Figure 1:
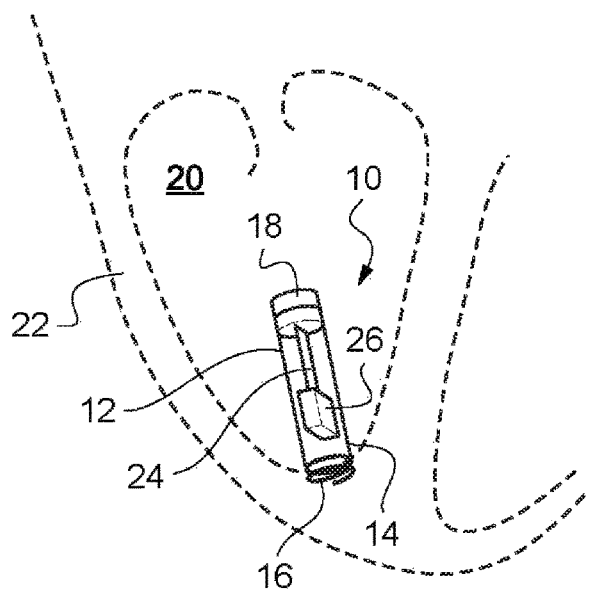
FIG. 1 illustrates a medical device of the leadless capsule type in its environment, implanted in the bottom of the right ventricle of a patient.

FIG. 1 shows a leadless capsule device 10 in a cardiac stimulation application.

The capsule 10 is made in the external form of an implant with an elongated cylindrical tubular envelope 12 enclosing the various electronic and power supply circuits of the capsule, as well as a pendular unit energy harvester. The typical dimensions of such a capsule are a diameter of the order of 6 mm for a length of about 25-40 mm.

The tubular envelope 12 has, at its front (distal) end 14, a protruding anchoring element, for example an helical screw 16, to hold the capsule on the implantation side. Other anchoring systems can be used, and do not modify in any way the implementation of the present invention. The opposite (proximal) end 18 of the capsule 10 is a free end, which is only provided with means for the link to a guide-catheter (not shown) or another implantation accessory usable at the time of implantation or explanation of the capsule and then disconnected from the latter.

In the example illustrated in FIG. 1, the leadless capsule 10 is an endocavitary implant implanted into a cavity 20 of the myocardium 22, for example at the apex of the right ventricle. As a variant, still in a cardiac stimulation application, the capsule may also be implanted on the interventricular septum or on an atrial wall, or also be an epicardial capsule placed on an external region of the myocardium, wherein these different implantation modes do not modify in any way the implementation of the present invention. To perform the detection/stimulation functions, an electrode (not shown) in contact with the cardiac tissue at the implantation site collects cardiac depolarization potentials and/or applies stimulation pulses. In some embodiments, the function of this electrode may be provided by the anchoring screw 16, which is then an active screw, electrically conductive and connected to the detection/stimulation circuit of the capsule.

The leadless capsule 10 is further provided with an energy harvesting module comprising an inertial pendular unit that oscillates, inside the capsule, following the various external stresses to which the capsule is subjected. These stresses may in particular result from: the movements of the wall to which the capsule is anchored, which are transmitted to the tubular body 12 by the anchoring screw 16; and/or the blood flow rate variations in the medium surrounding the capsule, which produce oscillations of the tubular body 12 at the rhythm of the heartbeats; and/or the various vibrations transmitted by the cardiac tissues.

The pendular unit may in particular be composed of a piezoelectric beam 24 clamped at one of its ends and whose opposite, free end is coupled to a mobile inertial mass 26. The piezoelectric beam 24 is an elastically deformable flexible beam that constitutes, with the inertial mass 26, a pendular system of the mass-spring type. Due to its inertia, the mass 26 subjects the beam 24 to a deformation of the vibratory type on either side of a neutral or non-deformed position corresponding to a stable rest position in the absence of any stress.

Actually, as for its mechanical behavior, this unit may be equated to a structure of the "clamped/free beam" type, having a natural frequency of oscillation, which is herein the frequency at which the mass-spring system oscillates. It will be noted that this natural frequency of oscillation, typically of the order of a few tens of hertz, is noticeably higher than the frequency of the external cyclic stresses that correspond to the frequency of the heartbeats (at most a few hertz).

Hence, at each heart contraction, the inertial mass (or other functionally similar mechanical component) will be stressed with a higher or lower amplitude, then the pendular system will oscillate several times with decreasing amplitudes (bounces characteristic of a damped periodic oscillation), and will finally stabilize up to the following heartbeat, where the stress/oscillation cycle will be similarly repeated.

The piezoelectric beam 24 further performs a function of mechanical-electrical transducer making it possible to convert into electrical charges the mechanical bending stress that is applied to it. These charges are collected by electrodes at the surface of the beam to produce an electrical signal that, after rectification, stabilization and filtering, will power the various electronic circuits of the capsule.

The beam is advantageously a beam of the bimorphous type, i.e. capable of generating energy on its two faces when subjected to a deformation. Theses transduction properties are typical of a piezoelectric material, such as the PZT ceramics or the mono-crystals of the PMN-PT, barium titanate or lithium niobate type.

Figure 2:
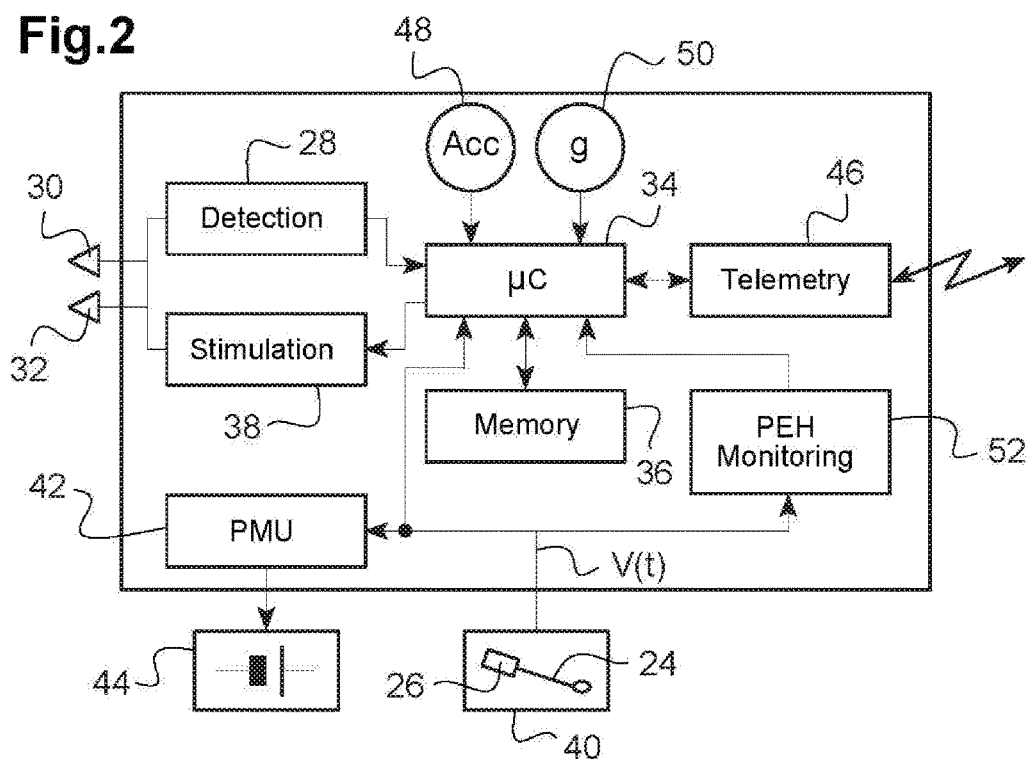
FIG. 2 schematically shows the main functional elements constitutive of the leadless capsule.

FIG. 2 is a synoptic of the various electric and electronic circuits integrated to the leadless capsule, shown as functional blocks. These circuits are advantageously made as an ASIC or a combination of ASICs. Block 28 represents a heart depolarization wave detection circuit, connected to a cathode electrode 30 in contact with the cardiac tissue and to an associated anode electrode 32, for example an annular electrode formed on the tubular body of the capsule. This detection block 28 comprises filters and means for the analog and/or digital processing of the collected signal. The so-processed signal is applied to the input of a microcalculator 34 associated with a memory 36. The electronic unit also includes a stimulation circuit 38 operating under the control of the microcalculator 34 to issue as needed myocardium stimulation pulses to the system of electrodes 30, 32.

An energy harvesting circuit 40 is further provided, composed of the pendular unit formed by the piezoelectric beam 24 and the inertial mass 30 described hereinabove with reference to FIG. 1. As the piezoelectric beam 24 also performs a function of mechanical-electrical transducer, it converts into electrical charges the mechanical stresses undergone and issues a variable electrical signal V(t) that is sent to an energy management circuit 42. This circuit 42 rectifies and regulates the signal V(t) so as to output a stabilized direct tension or current for powering the electronic unit and charging an integrated energy storage component 44, for example a rechargeable battery or a high-performance capacitor powering the electronic unit.

The leadless capsule further includes a telemetry emitter/receiver circuit 46 making it possible to establish a bidirectional communication with a remote device implanted into the patient or external to the latter, for example a programmer handled by a practitioner during a follow-up visit.

The leadless capsule is further provided with an accelerometer 48 adapted to measure the instantaneous acceleration undergone by the capsule, and hence by the beam 24 contained in the latter, at least according to a component oriented perpendicular to the surface of the beam, more precisely a component at the clamped end of the beam, which is perpendicular to the plane of the beam faces and perpendicular to its greater direction.

The leadless capsule may further advantageously, but optionally, comprise an angular acceleration sensor 50, providing a signal of instantaneous angular speed of rotation of the capsule, and hence of the beam, at least according to a component of rotation about an axis perpendicular to the plane of curvature of the beam, i.e. the plane including the neutral fiber and the center of curvature.

The accelerometer 48 and the angular acceleration sensor 50 are advantageously made as MEMS components, according to per se known techniques, for example that which is implemented within the inertial measurement units IMU made as a monolithic component.

Characteristically of the invention, the leadless capsule further comprises a circuit 52 for following up of the proper operation of the PEH, in particular for monitoring the integrity of the beam, interfaced with the microcalculator 34 and receiving the oscillating signal V(t) issued by the PEH 40, as well as the instantaneous acceleration signal provided by the accelerometer 48 and, as the case may be, the instantaneous angular speed signal provided by the angular speed sensor 50.

Figure 3:
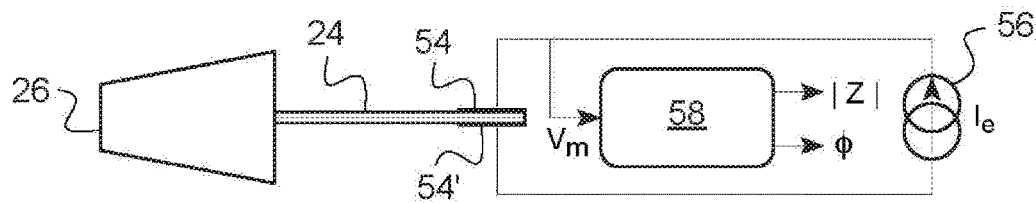
FIG. 3 schematically illustrates a known technique of measurement of the physical-electrical properties of a piezoelectric beam of a pendular unit.

FIG. 3 schematically illustrates a known technique of measurement of the physical-electrical properties of a piezoelectric beam of a pendular unit.

The evaluation of the physical and electromechanical parameters of a piezoelectric beam may be performed by several known manners, by static techniques (applying a known force to the free end of the beam then measuring the displacement of the latter to derive the stiffness thereof, and measuring the voltage across the electrode terminals to derive the mechanical-electrical conversion rate thereof) or dynamic techniques (making the beam vibrate and analyzing the alternating voltage issued).

The known technique illustrated in FIG. 3 is the so-called "complex impedance spectrometry", which consists in applying to the electrodes 54, 54' of the beam to be analyzed an alternating excitation current $I_e$ of known intensity and frequency, generated by a source of current 56. The beam, which is fixed to the test bench and not subjected to any external mechanical stress, enters into oscillation. The resulting alternating voltage $V_m$ is collected between the electrodes 54, 54' and analyzed by a synchronous detector 58 that outputs a complex impedance module value $|Z|=\mathrm{Abs}(V_m/I_e)$ and a phase-shift value $\Phi=\mathrm{Angle}(V_m, I_e)$. This test is reiterated for several different excitation frequencies, so as to be able to trace a characteristic curve of the beam giving Z and $\Phi$ as a function of the frequency.

Such a measurement technique is not conceivable for a piezoelectric beam of an already-implanted energy harvester, for which not only the beam is not physically accessible, but in which it is further continuously subjected to external stresses of high intensity and by nature indeterminable a priori.

Figure 4:
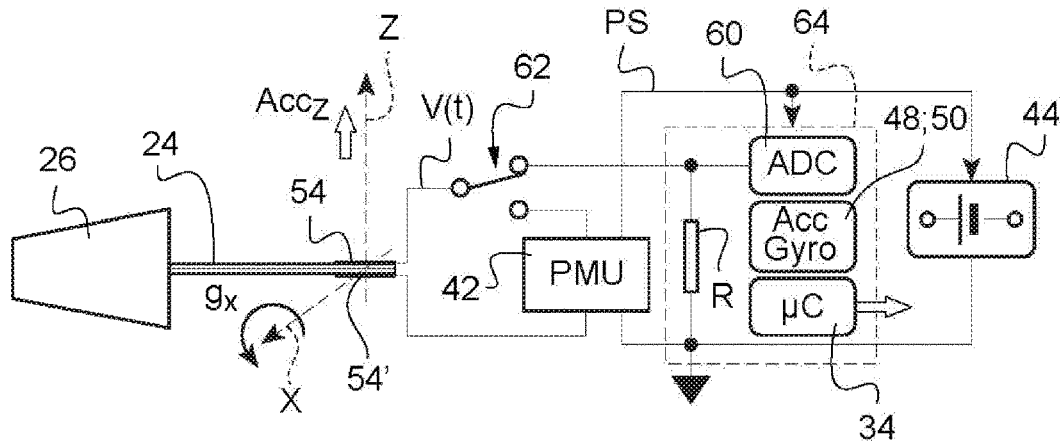
FIG. 4 schematically illustrates the technique according to the invention for measuring physical-electrical properties of a piezoelectric beam of a pendular unit of a PEH.
Figure 5:
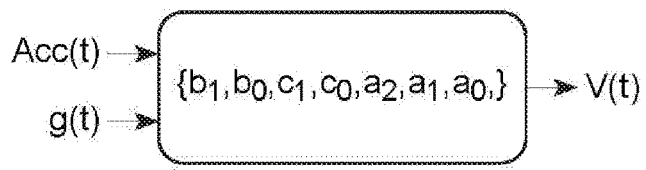
FIG. 5 schematically illustrates the various parameters and variables of the transfer function modelling the behavior of a piezoelectric beam such as a clamped/free beam stressed in bending.

The measurement technique according to the invention lies on a fully different concept, schematically illustrated in FIGS. 4 and 5.

The technique according to the invention consists in measuring the instantaneous acceleration undergone by the beam at the point of application of the external efforts that cause the oscillations of the pendular unit, i.e. at the clamped end of the beam. More precisely, the acceleration value measured is that of the component $Acc_z(t)$ in the direction Z perpendicular to the widest surface of the beam, i.e. the vertical direction in the plane of the figure, with the conventions of FIG. 4, in which the beam 24 is represented in profile, viewed from the side, and in which the plane of the figure is that in which the pendular beam 24-mass 26 unit oscillates.

This value $Acc_z(t)$ is output continuously by the acceleration sensor 48 equipping the capsule and integral with the latter. The variable signal $Acc_z(t)$ is sampled by the microcalculator 34 to provide a series of discrete sample values $Acc_z(s)$. The sampling frequency is preferably at least three times higher than a period of natural oscillation of the pendular unit (that typically oscillates at a frequency of a few tens of hertz), and very preferentially higher than or equal to 200 Hz.

Advantageously, it is provided to also measure the instantaneous angular speed undergone by the beam at its clamped end. More precisely, the angular speed value measured is that of the component of rotation $g_x(t)$ about an axis X perpendicular to the plane of curvature of the beam (the plane in which the pendular beam 24-mass 26 unit oscillates), i.e. perpendicular to the plane of the figure with the conventions of FIG. 4.

This value $g_x(t)$ is output continuously by the inertial unit 50 equipping the capsule and integral with the latter. The variable signal $g_x(t)$ is sampled by the microcalculator 34 to provide a series of discrete sample values $G_x(s)$ at the same rate as the acceleration samples $Acc_z(s)$.

In the following and unless otherwise mentioned, it will be considered that the angular speed is measured in addition to the acceleration, keeping in mind that this angular speed measurement is not itself necessary for the implementation of the invention, even if it allows increasing the accuracy of the analysis performed downstream and hence the quality of the results obtained, as will be explained hereinafter.

The voltage V(t) issued by the piezoelectric material of the beam 24 across the terminals 54, 54' of the beam by the oscillations of the pendular unit is also collected, digitized by an ADC converter 60, and sampled by the microcalculator 34 to provide a series of discrete sample values V(s) at the same rate as the acceleration $Acc_z(s)$ and angular speed $G_x(s)$ samples. The microcalculator 34 hence provides the beam integrity monitory circuit 52 with a series of successive samples $\{V(s), Acc_z(s), G_x(s)\}$.

Preferably, the energy management circuit PMU 42, which normally provides the power voltage PS of the device, is disconnected from the beam during the collection of the series of samples V(s), $Acc_z(s)$ and $G_x(s)$. This disconnection is operated by a switch 62 that, during a predetermined duration $T_m$, connects the terminals 54, 54' of the beam 24 between which the voltage V(t) is collected to a suitable resistive load R, which may simply be the input impedance of the circuit for measuring the voltage V(t).

The duration $T_m$, which is hence the duration during which the monitoring circuit 52 collects the data for evaluating the integrity of the beam, is preferably at least three times higher than the period of natural oscillation of the pendular beam 24-mass 26 unit (which is itself of the order of about 50 ms), and very preferentially at least higher than the duration of a mean cardiac cycle, hence at least higher than about 1 second.

From the hardware point of view, in a specific embodiment, the load R, the ADC circuit 60, the sensors 48 and 50 and the microcalculator 34 may be brought together within a specific module 64 for monitoring the integrity of the beam, dedicated to this function.

The dedicated specific module 64 may be an independent and autonomous module, or a module included in the electronic unit of an autonomous device such as a leadless capsule as herein described (or any other autonomous device, medical or not), or an integrated module located in the energy harvesting circuit PMU 42.

The specific module may further also include means for generating alerts in case of failure detection, and for wire-based or wireless communication to inform an application that uses the module about the structural condition of the energy harvester.

The output voltage V(t) provided by the piezoelectric beam is linked to the acceleration $Acc_z(t)$ and to the angular speed $g_x(t)$ undergone by this beam by a transfer function, schematized in FIG. 5, of the type:

$$V(t) = H_1 * Acc_z(t) + H_2 * g_x(t)$$

The Laplace transform in the time domain of this function is, in discrete time for a series of corresponding samples V(s), $Acc_z(s)$ and $G_x(s)$:

$$V(s) = b_1 s + b_0/s^3 + a_2 s^2 + a_1 s + a_0 Acc_z(s) c_1 s + c_0/s^3 + a_2 s^2 + a_1 s + a_0 G_x(s)$$

Such a modeling is per se known, in particular from:

[1] Erturk, A., & Inman, D. J. (2008), On Mechanical Modeling of Cantilevered Piezoelectric Vibration Energy Harvesters, *Journal of Intelligent Material Systems and Structures*, 19 (11), 1311-1325;

[2] Erturk A and Inman D J (2008), A Distributed Parameter Electromechanical Model for Cantilevered Piezoelectric Energy Harvesters, *Journal of Vibration and Acoustics*, 130(4): 041002;

[3] Erturk A, Renno J M and Inman D J (2009), Modeling of Piezoelectric Energy Harvesting from an L-Shaped Beam-Mass Structure with an Application to UAVs, *Journal of Intelligent Material Systems and Structures*, 20(5): 529-544; and

[4] Wickenheiser A M (2011), Design Optimization of Linear and Nonlinear Cantilevered Energy Harvesters for Broadband Vibrations, *Journal of Intelligent Material Systems and Structures*, 22(11): 1213-1225, to which reference can be made for further details and which are incorporated herein by way of reference.

Parameters $\{b_1, b_0, c_1, c_0, a_2, a_1, a_0\}$ are the modeling parameters characterizing the above function.

From a series of samples $\{V(s), Acc_z(s), G_x(s)\}$ obtained from measured values, these parameters $\{b_1, b_0, c_1, c_0, a_2, a_1, a_0\}$ may be determined, in particular, by application of known techniques of system identification applied to linear systems, as those described for example by

[5] Ljung L, Experiments With Identification of Continuous-Time Models, Proceedings of the 15th IFAC Symposium on System Identification, 2009, 1175-1180, to which reference can be made for further details and which is incorporated herein by way of reference.

Figure 6:
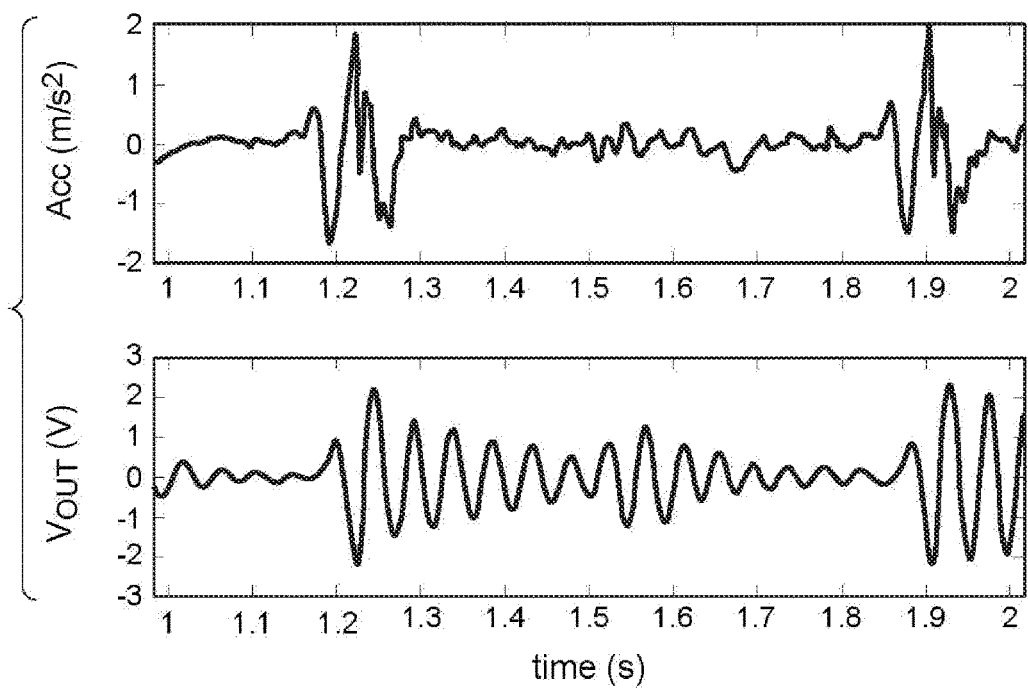
FIG. 6 is an example of a record of the variations of acceleration undergone by the piezoelectric beam during a cardiac cycle, with the corresponding issued output voltage reflecting in particular the damped oscillations of the electrical signal provided by the PEH.

FIG. 6 is an example of a record of the variations of acceleration $Acc_z(t)$ undergone by the piezoelectric beam 24 during a cardiac cycle, with the corresponding output voltage V(t) issued by the PEH, as measured across terminals 54, 54', which reflects the damped oscillations of the pendular beam 24-mass 26 unit at the natural oscillation frequency thereof between two successive heartbeats.

Figure 7:
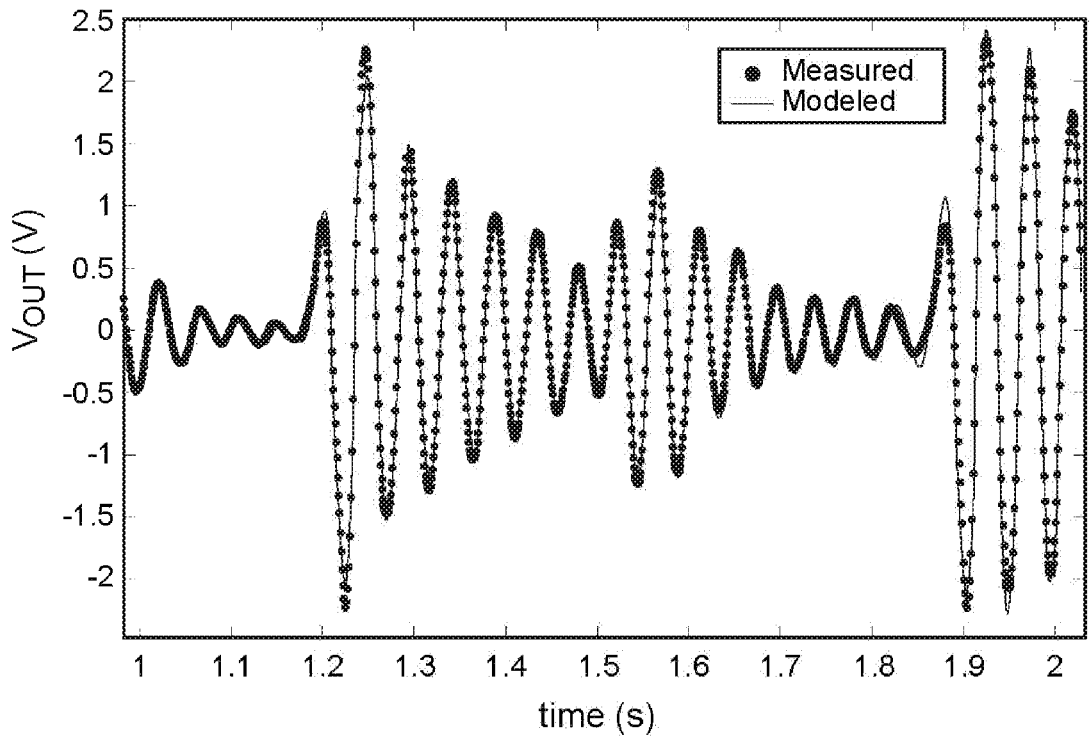
FIG. 7 is an example of a record of the variations of the output voltage signal provided by the PEH with, in superposition, the same variations calculated by application of a theoretical model.
Figure 8:
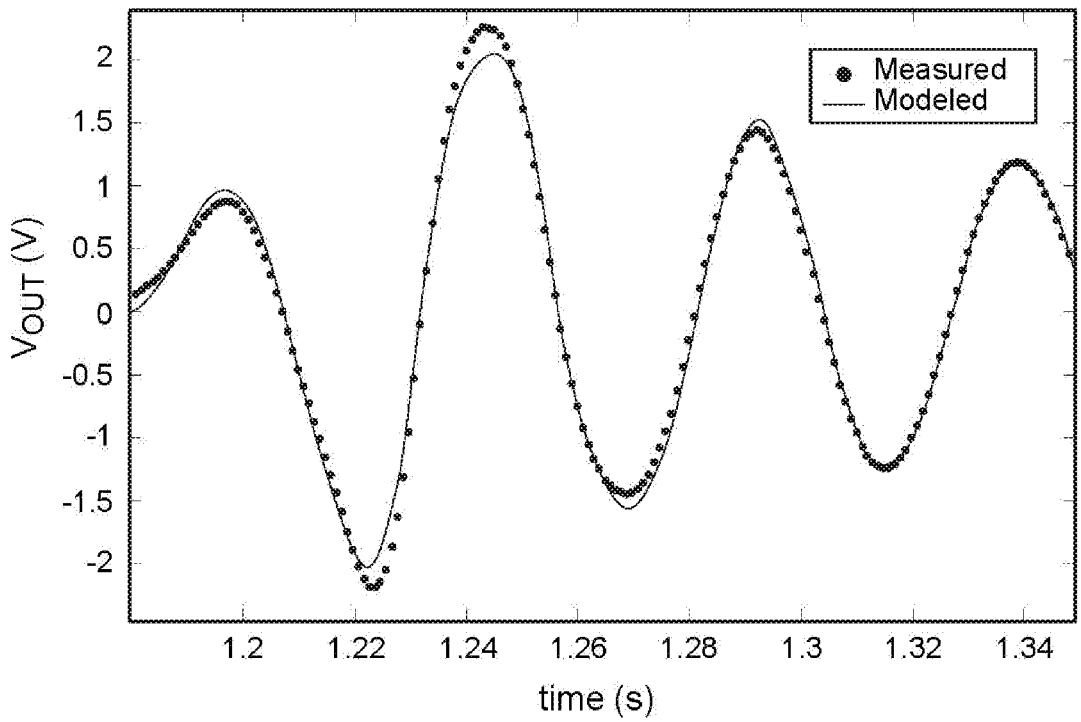
FIG. 8 is an enlarged view of the first oscillations of the signal of FIG. 7.

FIG. 7 (and FIG. 8 in enlarged view) shows the variations of the signal issued by the PEH over the successive oscillations of the inertial unit, with, in superimposition: the variations V(s) calculated by application of the above-mentioned theoretical model (at a sampling frequency of 1000 Hz, corresponding to the successive points), and the voltage variations V(t) really measured in practice (corresponding to the continuous line).

These records show the excellent fit of the theoretical model formulated hereinabove to the reality of the piezoelectric beam behavior. In practice, the overall quality of fit of the model to the reality is typically of the order of 85 to 95%.

If only the acceleration $Acc_z(t)$ is measured, without taking into account the angular speed $g_x(t)$, the above relation may be simplified by eliminating the second right term, which gives:

$$V(s) = \frac{b_1 s + b_0}{s^3 + a_2 s^2 + a_1 s + a_0} Acc_z(s)$$

In this case, the fit of the model to the reality of the beam behavior is lower, of the order of 70%, which may however be enough as a first approach for evaluating the PEH behavior and in particular the integrity of the beam.

The estimation of the modeling parameters $a_0$, $a_1$, $a_2$, $b_0$, $b_1$, $c_0$, $c_1$ (or $a_0$, $a_1$, $a_2$, $b_0$, $b_1$ in the simplified version that does not take into account the angular speed) from the samples V(s), $Acc_z(s)$ and $G_x(s)$ (or V(s) and $Acc_z(s)$ in the simplified version) makes it possible, in the first instance, to derive from these estimates a certain number of physical parameters specific to the pendular unit, in particular:

the resonance frequency $F_n$ of the pendular unit;
the quality factor Q of the pendular unit; and
the generalized coupling coefficient $\Theta$ of the pendular unit.

These parameters constitute as many metrics for evaluating the overall behavior of the considered PEH and detecting the appearance of a potential weakness or failure of the later. In particular:

the resonance frequency $F_n$ is a function of the beam stiffness and of the value of the mass 26: in case of a detachment of the mass 26 from the beam 24, or in case of a breaking of the beam 24, the frequency $F_n$ would be immediately affected in a manner that is easily detectable;

the quality factor Q reflects the quality of fixation of the beam clamped end to the inside of the capsule casing: if this fixation becomes looser, the quality factor will be affected; and the generalized coupling coefficient $\Theta$ reflects the overall quality of the piezoelectric material of the beam as well as the quality of adherence of the electrodes to the piezoelectric material: a degradation of this factor would indicate an ageing of the beam material and/or of the material/electrode interface.

Secondly, knowing the mass m of the seismic mass 26 of the pendular unit and the geometrical dimensions of the beam, it is possible to derive from the above-mentioned metrics $F_n$, Q and $\Theta$ further metrics which are more precisely representative of the integrity of the piezoelectric material, and hence of the potential ageing of the latter:

electrical capacitance C of the beam;
mechanical stiffness $E_p$ of the beam;
mechanical-electrical conversion coefficient $e_{31}$ of the beam.

These further metrics make it possible to evaluate the overall behavior of the piezoelectric material and to detect a potential weakness or failure thereof. In particular:

the electrical capacitance C is linked to the quality of the piezoelectric material and to the proper interfacing of the electrodes with this material: a significant variation of C could indicate a cracking of the piezoelectric material or a failure of the connection of the electrodes to the piezoelectric material, or a failure of the connection of the electronics to the electrodes;

the mechanical stiffness $E_p$ of the beam is an indicator of the mechanical fatigue of the beam;

the mechanical-electrical conversion coefficient $e_{31}$ is linked to the natural polarization of the piezoelectric material: a decrease or a loss of polarization leading to a decrease of the conversion yield of the PEH may then be early detected.

The various metrics linked to the PEH considered as a whole and/or more specifically to the beam, considered in isolation or in combination, are memorized in an history whose evolution over time is analyzed at periodic intervals to evaluate the "health condition" of the PEH and the evolution thereof over the long term.

Figure 9:
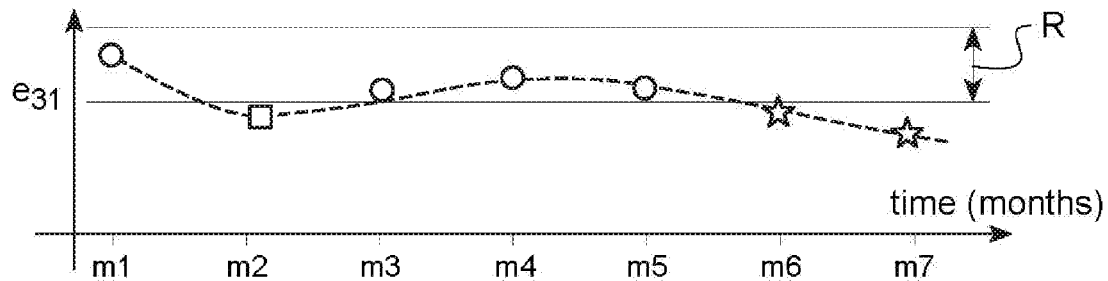
FIG. 9 is an example of long-term evolution of an indicator representative of a physical-electrical property of the beam, showing a progressive, proven, degradation of the integrity of the latter.

FIG. 9 accordingly illustrates the long-term variations of an indicator representative of a property of the beam, for example the mechanical-electrical conversion coefficient $e_{31}$. This example shows a progressive, proven, degradation of the integrity of the beam.

This metric (as well as other metrics such as $F_n$, C, $E_p$ . . . ) is measured on a periodical basis, for example every week or every month and the absolute values as well as their variations from one measure to the other are monitored and compared to threshold values.

When certain predetermined criteria are met, an alarm is triggered by the microcalculator 24 and sent by the telemetry circuit 46 to an external device to notify a significant evolution of the quality and the conversion yield of the PEH.

An alarm may for example be generated when one of the metrics (the square in FIG. 9) leaves a predetermined security range R, or when two consecutive values of this metric (the stars in FIG. 9) leave this same range. Other comparable criteria may be applied to the other metrics $F_n$, C, $E_p$ . . . , possibly with multiple criteria making it possible to analyze the cross-evolution of the various parameters, to modify the periodicity of the measurements in case of first alarm detected, etc.

Figure 10:
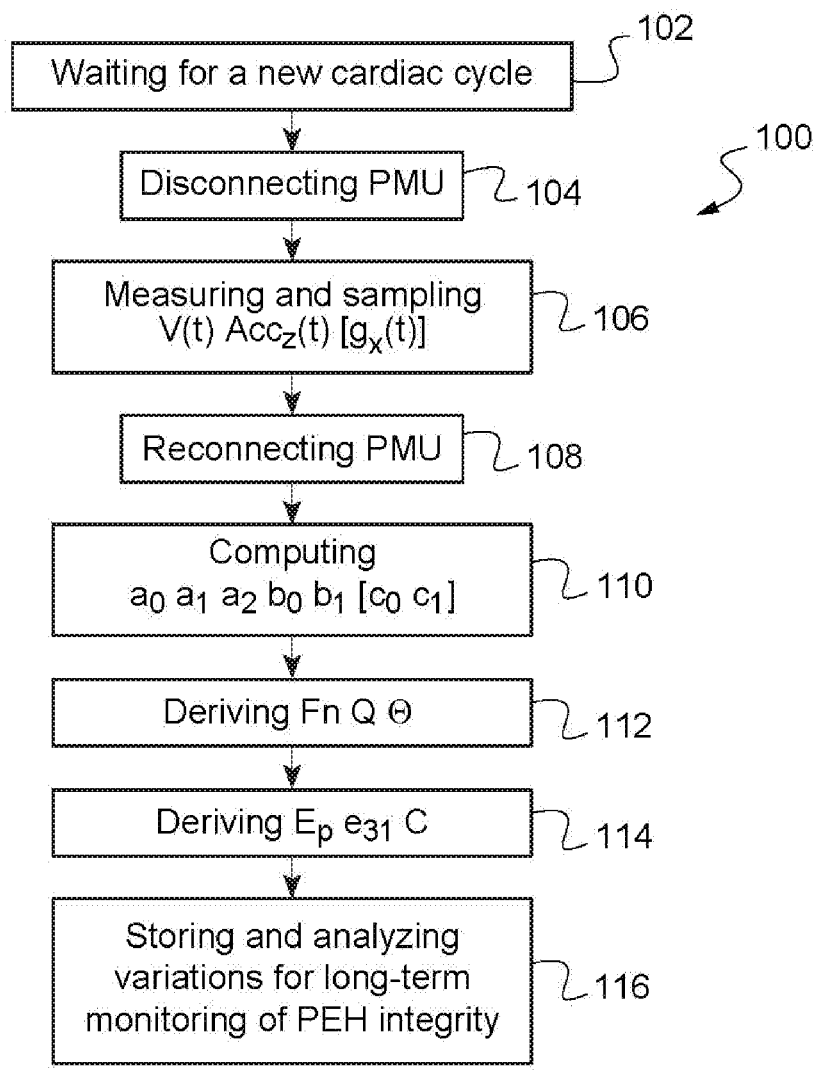
FIG. 10 is a flow diagram presenting the successive steps of an example of process for determining the physical-electrical parameters of the pendular unit and of the beam, representative of the level of integrity of the latter.

FIG. 10 is a flow diagram illustrating in a schematic and summarized manner the process 100 for determining the metrics representative of the physical and electrical parameters of the pendular unit and of the beam, in order to evaluate the level of integrity of the PEH as a whole and of the beam in particular.

At the beginning, the process waits for a new cardiac cycle (block 102) then, when a new cardiac cycle is detected, the power management circuit PMU is disconnected from the electrodes of the piezoelectric beam (block 104).

The device then measures the voltage V(t), acceleration $Acc_z(t)$ and, as the case may be, angular speed $g_x(t)$ values, and digitizes and samples these measurements to provide a series of samples V(s), $Acc_z(s)$ and $G_x(s)$ (block 106).

Once all the necessary samples collected, after a predetermined duration $T_m$, the power management circuit PMU is reconnected (block 108).

From the series of samples V(s), $Acc_z(s)$ and $G_x(s)$, the microcalculator estimates the modeling parameters $a_0$, $a_1$, $a_2$, $b_0$, $b_1$ and $c_1$, $c_0$ (block 110) and derives from these estimates the metrics $F_n$, Q and $\Theta$ representative of the condition of the PEH (block 112).

The metrics $E_p$, C and $e_{31}$ specific to the beam are then determined (block 114).

Finally, the various metrics obtained are memorized within the device, so as to be able to analyze their level and/or variations and to provide if need be an alarm in case of significant degradation of the integrity of an element of the PEH.

In a variant, in particular if the calculation means of the medical device are not powerful enough, the process halts at step 108 after the measurement of the voltage V(t), of the acceleration $Acc_z(t)$ and, as the case may be, of the angular speed $g_x(t)$, then stores these data V(t) $Acc_z(t)$ and $g_x(t)$ to send them afterwards by telemetry, via the emitter/receiver circuit 46, to a terminal or an external programmer to evaluate in non-real time the parameters of the harvester and the detection of the failures.

The above-described process 100 is triggered periodically, with a periodicity of for example a few hours to about ten days (in order not to compromise too much the energy harvesting performances or the implant consumption), and/or upon detection of a specific event, for example a significant drop of the mean power provided by the power management circuit 42.

The invention claimed is:

1. An energy harvesting module, comprising:
   a pendular unit subjected to external stresses applied to the module, the pendular unit comprising a beam that is elastically deformable in bending according to at least one degree of freedom, with a clamped end and an opposite free end coupled to an inertial mass;
   wherein the beam is a piezoelectric beam forming a mechanical-electrical transducer adapted to convert into an oscillating electrical signal a mechanical energy produced by oscillations of the pendular unit; and
   a power management circuit, adapted to rectify and regulate the oscillating electrical signal to output a stabilized direct power voltage or current,
   the energy harvesting module further comprising a circuit for monitoring the integrity of the beam, comprising:
   an acceleration sensor for providing an acceleration signal representative of the instantaneous acceleration of the beam in a direction perpendicular to a surface of the beam;
   a collecting and sampling circuit, adapted to receive the oscillating signal and the acceleration signal, and to provide a plurality of successive samples each containing an oscillating signal value associated with a concomitant acceleration value;
   a memory storing a transfer function describing the mechanical-electrical behavior of the beam,
   wherein said transfer function is a relation providing, for respective given values of a set of modelling parameters, an oscillating signal value as a function of a value of instantaneous acceleration of the beam; and
   a processor and a memory comprising instructions for causing the processor to execute a process comprising the following steps:
   a) receiving the plurality of said successive samples each containing an oscillating signal value associated with a concomitant acceleration value;
   b) applying these successive samples to said transfer function to derive therefrom a corresponding set of estimates of said modelling parameters from the oscillating signal and acceleration values of the successive samples; and
   c) deriving from said estimates of the modelling parameters at least one physical metric of the pendular unit and/or of the beam.

2. The module of claim 1, wherein the at least one physical metric is a metric of the group comprising:
   resonance frequency $F_n$ of the pendular unit;
   quality factor Q of the pendular unit;
   generalized coupling coefficient $\Theta$ of the pendular unit;
   electric capacitance C of the beam;
   mechanical stiffness $E_p$ of the beam; and
   mechanical-electrical conversion coefficient $e_{31}$ of the beam.

3. The module of claim 1, wherein
   the beam integrity monitoring circuit further comprises an angular speed sensor to provide an angular speed signal representative of the instantaneous angular speed of rotation of the beam about an axis perpendicular to a plane of bending of the beam, the transfer function is a relation further providing the oscillation signal value as a function of a value of instantaneous angular speed of the beam, the collecting and sampling circuit is adapted to further receive the angular speed signal, the successive samples provided by the collecting and sampling circuit each contain an oscillating signal value associated with concomitant acceleration and angular speed values, and at step b) the process derives the set of estimates of the modelling parameters from the oscillating signal acceleration and angular speed values of the successive samples.

4. The module of claim 1, wherein the beam integrity monitoring circuit further comprises a switch for disconnecting said power management circuit during a predetermined period of activation of the collecting and sampling circuit.

5. The module of claim 4, wherein said predetermined period of activation of the collecting and sampling circuit is at least three times longer than a period of natural oscillation of the pendular unit.

6. The module of claim 1 or claim 3, wherein, at step c), the process comprises the following steps:
c1) deriving a set of first metrics specific to the pendular unit from said estimates of the modelling parameters; and
c2) deriving from a set of second metrics specific to the beam from said first metrics determined at step c1).

7. The module of claim 1, wherein the process further comprises:
memorizing, into an history, the values of the first metrics determined at step c1) and/or of the second metrics determined at step c2).

8. The module of claim 7, wherein the process further comprises:
comparing the first metrics determined at step c1) and/or the second metrics determined at step c2) with respect to respective reference values.

9. The module of claim 7, wherein the process further comprises:
analyzing the evolution over time of the first metrics determined at step c1) and/or the second metrics determined at step c2).

10. The module of claim 7, wherein the sampling frequency of the collecting and sampling circuit is higher than 200 Hz.

11. The module of claim 1,
wherein the module is incorporated into an autonomous device housing, in a device body: an electronic unit; said energy harvesting module; and an energy storage component for powering the electronic unit,
and wherein said stabilized direct voltage or current output by the power management circuit is used to power the electronic unit and/or to charge the energy storage component.

12. The module of claim 11, wherein the autonomous device is an active medical device.

13. The module of claim 12, wherein the active medical device is an implantable autonomous capsule, comprising a capsule body provided with an element for its anchoring to a wall of a patient's organ,
and wherein said external stresses to which is subjected the pendular unit are stresses applied to the capsule body under the effect of movements of said wall and/or of blood flow rate variations in the surrounding medium.

* * * * *